(12) United States Patent
Suva et al.

(10) Patent No.: US 8,268,573 B2
(45) Date of Patent: *Sep. 18, 2012

(54) COMPOSITIONS AND METHODS FOR MONITORING BREAST CANCER TREATMENT

(75) Inventors: Larry J. Suva, Little Rock, AR (US); V. Suzanne Klimberg, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 345 days.

This patent is subject to a terminal disclaimer.

(21) Appl. No.: 12/538,987

(22) Filed: Aug. 11, 2009

(65) Prior Publication Data

US 2010/0129918 A1    May 27, 2010

Related U.S. Application Data

(63) Continuation of application No. 11/615,123, filed on Dec. 22, 2006, now Pat. No. 7,601,800, which is a continuation of application No. 10/903,500, filed on Jul. 30, 2004, now Pat. No. 7,186,517.

(60) Provisional application No. 60/492,162, filed on Aug. 1, 2003.

(51) Int. Cl.
*G01N 33/483* (2006.01)
(52) U.S. Cl. ............ 435/7.21; 435/366; 250/287
(58) Field of Classification Search .......... None
See application file for complete search history.

(56) References Cited

U.S. PATENT DOCUMENTS

| 5,248,697 | A | 9/1993 | Wilmore |
| 5,438,075 | A | 8/1995 | Skubitz et al. |
| 5,576,301 | A | 11/1996 | Hymer et al. |
| 7,186,517 | B2 | 3/2007 | Suva et al. |
| 7,601,800 | B2 | 10/2009 | Suva et al. |
| 2002/0147156 | A1 | 10/2002 | Petit, II et al. |
| 2003/0099722 | A1 | 5/2003 | Baxter |
| 2005/0042700 | A1 | 2/2005 | Suva et al. |
| 2007/0196887 | A1 | 8/2007 | Suva et al. |

FOREIGN PATENT DOCUMENTS

WO    WO-2005/012904 A1    2/2005

OTHER PUBLICATIONS

"U.S. Appl. No. 10/903,500, Amendment and Response filed Jun. 14, 2006 to Non-Final Office Action mailed Mar. 8, 2006", 7 pgs.
"U.S. Appl. No. 10/903,500, Non-Final Office Action mailed Mar. 8, 2006", 9 pgs.
"U.S. Appl. No. 10/903,500, Notice of Allowance mailed Sep. 29, 2006", 9 pgs.
"U.S. Appl. No. 10/903,500, Response to Restriction Requirement mailed Dec. 8, 2005", 6 pgs.
"U.S. Appl. No. 10/903,500, Restriction Requirement mailed Jul. 26, 2007 in U.S. Appl. No. 11/615,123", 6 pgs.
"U.S. Appl. No. 10/903,500, Restriction Requirement mailed Nov. 1, 2005", 6 pgs.
"U.S. Appl. No. 11/615,123, Non-Final Office Action mailed Aug. 7, 2008", 7 Pgs.
"U.S. Appl. No. 11/615,123, Non-Final Office Action mailed Nov. 1, 2007", 11 Pages.
"U.S. Appl. No. 11/615,123, Notice of Allowance mailed Jun. 3, 2009", 7 pgs.
"U.S. Appl. No. 11/615,213, Response filed May 1, 2008 to Non-Final Office Action mailed Nov. 1, 2007", 12 pgs.
"PCT Application No. PCT/US2004/024928, International Preliminary Report on Patentability mailed Feb. 6, 2006", 9 pgs.
"PCT Application No. PCT/US2004/024928, International Search Report and Written Opinion mailed Dec. 1, 2005", 14 pgs.
Burnet, N. G, et al., "Describing Patients' Normal Tissue Reactions: concerning the possibility of individualising radiotherapy dose prescriptions based on Potential Predictive assays of normal Tissue Radiosensitivity", *Int. J. Cancer (Pred. Oncol.)*,79, (1998), 606-613.
Geara, F., et al., "Intrinsic Radiosensitivity of normal human Fibroblasts and Lymphocytes after hign- and low-dose-rate Irradiation", *Cancer Research*, 52, (Nov. 15, 1992), 6348-6352.
Hellman, S., et al., "Principles of Cancer Management: Radiation Therapy", *Cancer, Principles and Practice of Oncology*, Chapter 16, Published by Lippincott, Williams & Wilkins, (2001), 265.
Mattison, P., et al., "Serum Proteins as Tumor Markers for Breast Cancer", *British Journal of Cancer*, 43, (1981), 542-545.
Raida, M., et al., "Liquid Chromatography and Electrospray Mass Spectrometric Mapping of Peptides from Human Plasma Filtrate", J Am Soc Mass Spectrum (10), (1999), 45-54 pgs.
Skubitz, K. M, et al., "Oral glutamine to prevent chemotherapy induced stomatitis: A pilot study", *Journal of Laboratory & Clinical Medicine*, 127, (Feb. 1996), 223-228.

*Primary Examiner* — Anand Desai
(74) *Attorney, Agent, or Firm* — Schwegman Lundberg & Woessner, P.A.

(57) ABSTRACT

The present invention provides compositions and processes for preparing the same wherein the compositions are useful for monitoring breast cancer treatment.

6 Claims, 2 Drawing Sheets

SEQUENCE LISTING

```
<160> NUMBER OF SEQ ID NOS: 2

<210> SEQ ID NO 1
<211> LENGTH: 11
<212> TYPE: PRT
<213> ORGANISM: Homo sapiens
<220> FEATURE:
<221> NAME/KEY: SITE
<222> LOCATION: 3
<223> OTHER INFORMATION: Xaa = Isoleucine or Leucine
<220> FEATURE:
<221> NAME/KEY: SITE
<222> LOCATION: 7
<223> OTHER INFORMATION: Xaa = Glutamine or Lysine
<220> FEATURE:
<221> NAME/KEY: SITE
```

```
<222> LOCATION: 10
<223> OTHER INFORMATION: Xaa = Isoleucine or Leucine

<400> SEQUENCE: 1

Ala Asp Xaa Ala Gly His Xaa Glu Val Xaa Arg
 1               5                   10

<210> SEQ ID NO 2
<211> LENGTH: 12
<212> TYPE: PRT
<213> ORGANISM: Homo sapiens
<220> FEATURE:
<221> NAME/KEY: SITE
<222> LOCATION: 6
<223> OTHER INFORMATION: Xaa = Isoleucine or Leucine
<220> FEATURE:
<221> NAME/KEY: SITE
<222> LOCATION: 8
<223> OTHER INFORMATION: Xaa = Isoleucine or Leucine
<220> FEATURE:
<221> NAME/KEY: SITE
<222> LOCATION: 11
<223> OTHER INFORMATION: Xaa = Isoleucine or Leucine

<400> SEQUENCE: 2

His Gly Thr Val Val Xaa Thr Xaa Gly Gly Xaa Lys
 1               5                   10
```

COMPOSITIONS AND METHODS FOR MONITORING BREAST CANCER TREATMENT

CLAIM OF PRIORITY

This application is a continuation application of U.S. patent application Ser. No. 11/615,123, filed Dec. 22, 2006, now issued as U.S. Pat. No. 7,601,800, which claims priority under 35 U.S.C. 120 or 35 U.S.C. 365(c) from continuation application U.S. patent application Ser. No. 10/903,500, filed Jul. 30, 2004, now issued as U.S. Pat. No. 7,186,517 B2, which claims priority under 35 U.S.C. §119(e) from U.S. Provisional Application Ser. No. 60/492,162 filed Aug. 1, 2003, which applications are incorporated herein by reference.

BACKGROUND OF THE INVENTION

Glutamine supplementation has been shown to prevent induction of mammary (breast) cancer in rats by the carcinogen 7,12-dimenthyl-benz[a]anthracene (DMBA) (Feng, Z., et al., *Surgical Forum* 47:524-526 (1996)). It has also been shown to enhance the effectiveness of methotrexate chemotherapy in rats (Klimberg, V. S., et al., *J. Parenteral and Enteral Nutrition* 16:83 S-87S (1992)).

Glutamine supplementation has been shown to provide numerous other benefits, including stimulation of certain cells of the immune system and general promotion of cellular growth. Depletion of glutamine results in atrophy of epithelial tissue, with associated bacterial translocation. Clinical supplementation of glutamine reduces epithelial atrophy and accelerates recovery of damaged epithelium.

Dietary glutamine supplementation has been proposed for the treatment of patients recovering from surgery or suffering from sepsis, inflammation, burns, or trauma. Topical administration, usually in the form of a "swish and swallow" solution for oral use can be effective to repair the damaged epithelial tissue of mouth or esophageal sores in many patients who have undergone bone marrow transplantation or chemotherapy. (Skubitz, et al., *J. Lab. Clin. Med.* (1996) 127(2): 223-8; Anderson, et al., *Bone Marrow Transplant* (1998) 22(4): 339-44.)

Methods are needed to monitor the effectiveness of glutamine supplementation in order to tailor dosing and plan associated treatments, such as radiation therapy and chemotherapy, that may comprise glutamine supplementation.

SUMMARY OF THE INVENTION

The present invention provides a novel human protein. The level of the protein increases in vivo in breast cancer patients during treatment by radiation therapy and glutamine supplementation, and decreases when glutamine supplementation is stopped. Tracking the level of the protein in serum may be used to monitor a patient's response to glutamine supplementation.

Accordingly, the invention provides an isolated and purified human serum protein characterized in that the protein: (a) has a molecular weight of approximately 9.29 kDa; and (b) increases in concentration in the serum of a woman afflicted with breast cancer during treatment by oral administration of glutamine and radiation therapy.

The invention also provides an isolated and purified protein fraction from serum of a human prepared by (a) administering glutamine to the human; (b) fractionating serum proteins of the human to isolate a protein fraction of approximately 9.29 kDa molecular weight.

The invention also provides an isolated and purified protein from that protein fraction, where digestion of the isolated and purified protein with trypsin generates a fragment with a molecular weight of approximately 1581 daltons and/or a fragment with a molecular weight of approximately 1709 daltons.

In one embodiment of the invention, the protein includes an amino acid sequence such as SEQ ID NO:1, SEQ ID NO:2, or a combination thereof.

Also provided is a therapeutic composition that has a protein of the invention.

The invention also provides a method of monitoring the effectiveness of glutamine administration to protect breast tissue against radiation injury, the method comprising: monitoring the concentration of a 9.29 kDa protein in serum of a human afflicted with breast cancer, before, during, and after the administration of glutamine and radiation therapy.

The invention also provides a method of monitoring a response to glutamine administration (e.g., supplementation), the method comprising: monitoring the concentration of a 9.29 kDa protein in serum of a human before, during, and after glutamine administration.

DETAILED DESCRIPTION

Definitions

Figure 1:
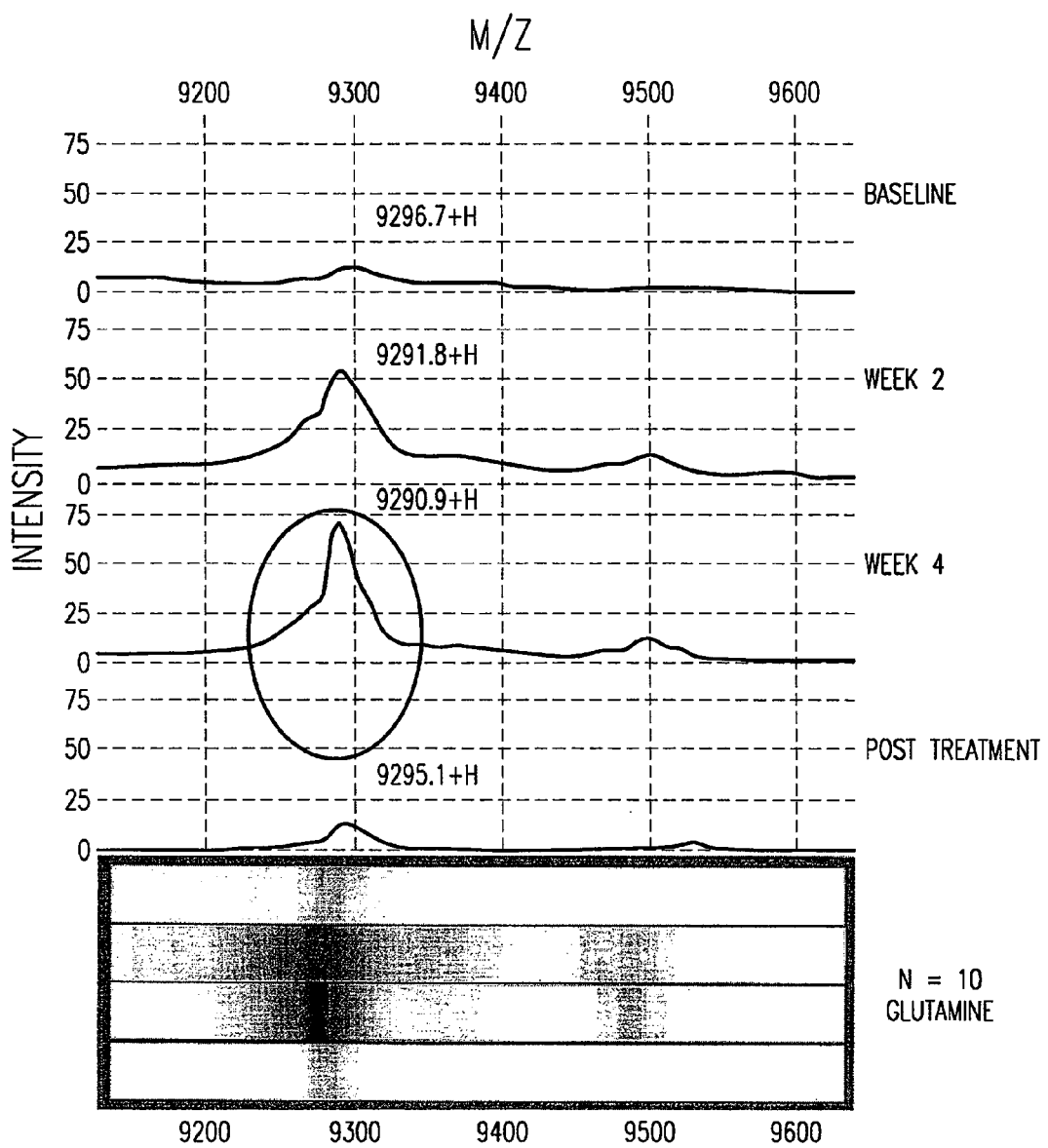
FIG. 1 shows the time course of appearance and disappearance of serum proteins in the molecular weight range of 9100 to 9650 in serum samples taken from one of ten women (N=10) undergoing radiation therapy and receiving oral glutamine (AES-14) supplementation. The lower portion of the figure is a visual representation of the data in the mass spectrometry scans of the upper portion of the figure to appear like 15 an SDS-PAGE

The term "or" as used herein, is both inclusive and exclusive, i.e., should be understood as "and/or."

The terms "isolated and purified protein" and "isolated and purified protein fraction" as used herein refer to a protein or protein fraction that is isolated and purified to any degree. That is, in an "isolated and purified protein" or "isolated and purified protein fraction" the desired protein or group of proteins constitute a greater fraction of the total protein than they do in the natural state in the mammal.

DESCRIPTION

It is believed that expression of the human protein described herein increases in vivo in concentration in response to administering glutamine to the patient. Thus, the protein may be at least partially responsible for the beneficial effects of glutamine, such as protecting against radiation damage to skin or breast tissue, enhancing natural killer cell activity, and promoting healing of damaged mucosal tissue associated with mucositis (Example 2 below; Fahr, M. J., et al., J. Parenteral and Enteral Nutrition 18:471-476 (1994); Skubitz, et al., *J. Lab. Clin. Med.* (1996) 127(2):223-8; U.S. Pat. No. 5,545,668).

Some of the uses of glutamine supplementation are described in U.S. provisional patent application Ser. No. 60/400,446; U.S. patent application Ser. No. 10/633,402; U.S. patent application Ser. No. 09/993,465, now U.S. Pat. No. 6,734,170; U.S. Pat. No. 5,438,075; and International (PCT) patent application PCT/US03/23987 titled "Improved Treatment of Cancer with Glutamine" (V. Suzanne Klimberg et al., filed Jul. 31, 2003). These uses include the use of administered glutamine (a) to enhance the effectiveness of radiation therapy or chemotherapy against cancer, (b) to alleviate or prevent mucositis, (c) to prevent metastasis in a mammalian subject afflicted with cancer, (d) to prevent recurrence of cancer in a mammalian subject in remission from cancer or undergoing anticancer therapy, (e) to inhibit the onset of cancer in a mammalian subject at risk of developing cancer, (f) to protect mucosal or non-mucosal (e.g., skin or breast tissue) tissue against damage for radiation therapy, (g) to protect mucosal or non-mucosal tissue (e.g., skin or breast tissue) against damage from chemotherapy, (h) to prevent pain arising from a non-mucosal tissue caused by chemotherapy or radiation therapy, (i) to promote healing of skin damaged by wound, injury or infection, (j) to enhance the effectiveness of chemotherapy or radiation therapy, (k) to increase the therapeutic index of chemotherapy or radiation therapy, (l) to promote apoptosis of cancer cells, or (m) to enhance natural killer cell activity.

Glutamine can be administered parenterally (e.g., intravenously, topically, or enterally), or orally. In one embodiment of the invention, it is administered orally. Administering glutamine in an aqueous solution comprising a carbohydrate, such as a saccharide, has been found to enhance the absorption of glutamine over the absorption of glutamine administered without carbohydrate (U.S. patent application Ser. No. 09/993,465, now U.S. Pat. No. 6,734,170; U.S. Pat. No. 5,438,075). Accordingly, in one embodiment, the glutamine is administered to a mammalian subject in a composition containing carbohydrate in an amount sufficient to enhance absorption of the glutamine by the subject.

The serum protein or proteins described herein that increase during treatment of breast cancer patients with glutamine supplementation and radiation therapy have a molecular weight of about 9.29 kDa. Specifically, the protein or proteins have a molecular weight in the range of about 9.24 to 9.34 kDa, for example, in the range of about 9.28 to 9.31 kDa.

In a particular embodiment, the serum protein that increases in response to glutamine supplementation, upon digestion with trypsin, generates a fragment that in electrospray mass spectrometry has an m/z of about 1581 and/or a fragment with an m/z of about 1709. That is, the molecular weights of the fragments are approximately 1581 and/or 1709 daltons.

To isolate the protein fraction or the isolated protein, serum proteins can be fractionated based on size. For instance, they can be fractionated by size exclusion chromatography. In one embodiment, the serum proteins are fractionated by Serum Enhanced Laser Desorption Ionization (SELDI)-mass spectrometry (MS). In this process, the serum proteins are adhered to a solid substrate (e.g., a SELDI chip) and then desorbed from the substrate and separated on the basis of size-to-charge ratio by SELDI-MS.

The glutamine-responsive serum protein can be used to monitor the effectiveness of glutamine administration, e.g., supplementation, or to monitor a response to glutamine administration. For instance, tracking the protein's concentration can be useful to monitor the effectiveness of glutamine administration (a) to enhance the effectiveness of radiation therapy or chemotherapy against cancer, (b) to alleviate or prevent mucositis, (c) to prevent metastasis in a mammalian subject afflicted with cancer, (d) to prevent recurrence of cancer in a mammalian subject in remission from cancer or undergoing anticancer therapy, (e) to inhibit the onset of cancer in a mammalian subject at risk of developing cancer, (f) to protect mucosal or non-mucosal (e.g., skin or breast tissue) tissue against damage for radiation therapy, (g) to protect mucosal or non-mucosal tissue (e.g., skin or breast tissue) against damage from chemotherapy, (h) to prevent pain arising from a non-mucosal tissue caused by chemotherapy or radiation therapy, (i) to promote healing of skin damaged by wound, injury or infection, (j) to enhance the effectiveness of chemotherapy or radiation therapy, (k) to increase the therapeutic index of chemotherapy or radiation therapy, (l) to promote apoptosis of cancer cells, or (m) to enhance natural killer cell activity.

In treatment of a group of breast cancer patients, the amount of the 9.29 kDa protein increased approximately 3-fold in the first two weeks of treatment with glutamine supplementation and radiation therapy, and then returned to near the baseline value within one week following discontinuation of glutamine. Accordingly, if the concentration of the protein does not increase to at least 2- to 5-fold in the first two weeks of glutamine supplementation, this is an indication that glutamine supplementation may not be having the desired effect. Accordingly, it may be advisable to increase the dose of glutamine. It may also be advisable if the patient is receiving chemotherapy or radiation therapy to, for instance, reduce the dose of chemotherapy or radiation therapy in order to reduce the risk of side effects such as mucositis or damage to breast tissue or skin.

The invention will now be further illustrated by the following non-limiting Examples.

EXAMPLES

Example 1

Evaluation of Cellular Uptake of Glutamine in Combination With Sucrose and Sorbitol The composition of the present invention has been shown to improve solubility and cellular absorption of an amino acid, glutamine, into human gastrointestinal epithelial cells, as illustrated in the following example.

1. Materials and Methods

Distilled, deionized water (107 ml) was added to 207 grams of a dry mixture of sucrose, sorbitol, and glutamine with excipients (Aesgen-14) as listed in Table 1.

TABLE 1

| Aesgen-14 (AES-14) | | | |
|---|---|---|---|
| L-glutamine | 240.0 Kg | 57.94 w %* | 50.00% w/v** |
| Sucrose | 144.0 Kg | 34.77 w % | 30.00% w/v |
| Crystalline Sorbitol | 13.44 Kg | 3.24 w % | 2.80% w/v |
| Glycerin | 14.0 Kg | 2.92 w % | 2.52% w/v |
| Sodium Phosphate Monobasic (Anhydrous) | 2.6 Kg | 0.63 w % | 0.54% w/v |
| Avicel Cellulose Gel Type CL-611 | 874.0 g | 0.18 w % | 0.17% w/v |
| Citric Acid (Anhydrous) | 280.0 g | 0.07 w % | 0.06% w/v |
| Xanthan Gum | 230.0 g | 0.05 w % | 0.04% w/v |

TABLE 1-continued

| Aesgen-14 (AES-14) | | | |
|---|---|---|---|
| Carrageenan | 230.0 g | 0.05 w % | 0.04% w/v |
| Artificial Flavor | 230.0 g | 0.05 w % | 0.04% w/v |
| Methylparaben | 207.0 g | 0.04 w % | 0.04% w/v |
| Potassium Sorbate Powder | 180.0 g | 0.04 w % | 0.04% w/v |
| 30% Simethicone Emulsion | 115.0 g | 0.02 w % | 0.02% w/v |

*Weight percents are expressed as percent of total weight of dry ingredients for reconstitution with water in a 240 ml bottle.
**Weight/volume percents are expressed as percent of total volume in aqueous mixture.

As a control, 200 milliliters of distilled, deionized water was added to 50 grams of L-glutamine (Ajinomoto, Raleigh N.C.) and mixed by agitation. Both samples were allowed to stand for 1 day at room temperature. The supernatant was decanted from the residue and used for the cellular uptake determination.

On Day 1, cells from a human gastrointestinal epithelial cell line (CaCo) were plated at a density of $0.5 \times 10^6$ cells per well in a 6-well tissue culture dish. On Day 2, culture media was replaced with either normal growth medium or medium deficient in L-glutamine.

On Day 3, cells cultured in both normal growth medium ("normal") and L-glutamine deficient growth medium ("starved") were evaluated for comparison of glutamine uptake using the Aesgen-14 solution in parallel with the L-glutamine solution, according to the following protocol: Two milliliters of test material (either Aesgen-14 or L-glutamine solution) was added to the appropriate wells, then incubated at 37 EC. At time points 0, 10, 20, 40, and 60 seconds, the test material was aspirated and the cells washed three times (3×) with chilled (4 EC) phosphate buffered saline (PBS), followed by the addition of 1.0 ml of perchloric acid. Cells were harvested by scraping, then aspirated by pipet into a 1.7 ml tube.

The harvested cells were sonicated for 10 seconds, and 500:1 of sonicated cells were transferred into a 1.7 ml tube. The perchloric acid was neutralized by the addition of 130:1 of 2M $KHCO_3$, and the resulting mixture was frozen overnight at −80 EC.

Upon thawing, the sample was centrifuged for 10 minutes at 14,000 rpm and the supernatants were transferred to new 1.7 ml tubes and frozen at −80 EC. The resulting clarified samples were thawed and diluted 1:3 with deionized water. Fifty microliters were withdrawn, added to 10 microliters complete o-phthaldialdehyde (Sigma P-0532), and mixed by agitation. After incubation for two minutes at room temperature, a 20:1 sample was injected on a Hypersil® C18 Elite 5:m HPLC column using 70:30 acetonitrile:water as the mobile phase. Glutamine levels, measured as :g/ml, were detected at 340 nm.

2. Results

Results are shown in Table 2 as :g/ml mean cellular glutamine uptake:

TABLE 2

| | Incubation Time (Seconds) | | | | |
|---|---|---|---|---|---|
| | 0 | 10 | 20 | 40 | 60 |
| Normal cells + Aesgen 14 | 1.00 | 1568.55 | 900.60 | 1185.88 | 1765.13 |
| Normal cells + L-glutamine | 3.53 | 10.30 | 2.48 | 3.23 | 4.85 |
| Starved cells + Aesgen 14 | 0.00 | 613.10 | 672.93 | 1213.40 | 1053.85 |
| Starved cells + L-glutamine | 1.33 | 1.43 | 1.49 | 2.23 | 49.96 |

As summarized above, glutamine uptake is significantly increased in both normal cells (363×) and in starved cells (21×) in cells treated with Aesgen-14 (AES-14) as compared to cells treated with aqueous L-glutamine alone.

Example 2

Oral AES-14 Protects Breast Tissue Against Radiation Injury

The cosmetic result after breast conservation therapy (BCT) is limited, in part, by radiation injury to the skin and surrounding tissue. In preclinical studies, glutamine (GLN) has been shown to significantly reduce both acute and chronic radiation injury to the small bowel possibly through upregulation of glutathione (GSH) metabolism. Oral administration of AES-14 to provide GLN doubles normal intracellular breast GSH without increasing GSH in breast tumor tissue. We therefore hypothesized that GLN may safely prevent radiation injury to normal breast tissue in BCT patients.

This theory was tested in two parts. First, biopsies from human breast tumors before and after 3 days of oral AES-14 indicated no significant change in intracellular tumor GSH. A Phase III pilot study in which 17 patients were randomized to oral AES-14 (30 gm GLN/day, approximately 0.5 gm GLN/kg/day) or placebo from one week prior until one week after radiation therapy (5,000 cGy) was performed. Patients were followed weekly for 7 weeks and every 3 months for 2 years for acute and chronic radiation injury using the RTOG scales, skin biopsy at 0 and 7 weeks, GLN and GSH levels, US, mammogram density, lymphedema, quality of life and performance status.

The RTOG acute radiation morbidity scoring criteria for skin ranges from 0 (no change) to 4 (necrosis). A score of 2 (moist desquamation) was considered failure of treatment. Patients receiving oral AES-14 scored an average of 0.9±0.2, SEM compared to 1.4±0.2 in the placebo group. All patients in the placebo group reached a score of 2 or greater during the first 7 weeks. Two of 8 placebo patients required radiation therapy delay. Another patient scored 3 of 4 but did not delay radiation. Only 4 of 9 patients in the AES-14 group scored a high of 2, none a 3 (p=0.03 AES-14 vs. placebo, Fisher Exact). At 12 months, 4 of 8 patients in the placebo group complained of pain for which 3 required narcotics, 6 of 8 had significant edema, and 4 of 8 marked increased density and firmness of the radiated breast. In the AES-14 group 2 of 9 complained of mild pain not requiring narcotics, none had edema, and one patient had minimal increased density of the breast (p=0.01, AES-14 vs. placebo, Fisher Exact). At 2 year follow-up, 2 in the placebo group had local recurrence and none in the GLN group. Cosmetic scores averaged excellent (9.2±0.6) in the AES-14 group versus fair to good (7.3±1.0) in the placebo group.

The results of this pilot study suggest that oral GLN supplementation is a safe and effective way to reduce both acute and chronic radiation morbidity to the breast and may improve cosmesis.

Example 3

A 9.3 kDa Protein that Increases in Concentration in Response to Glutamine Supplementation Methods:

Sixteen breast cancer patients treated with radiation therapy were randomized to receive oral supplemental glutamine (AES-14) or a placebo. Ten of the sixteen women received AES-14 (30 g glutamine per day, approximately 0.5 g glutamine/kg/day) from one week prior to initiating radiation therapy (5,000 cGy) until one week after completing radiation therapy. Six patients received placebo. Serum was collected from each patient before beginning glutamine supplementation (Baseline), at two and four weeks after initiating glutamine supplementation, and one week after stopping glutamine supplementation (Post Treatment in FIG. 1).

Serum proteins from each sample were analyzed by SELDI-MS. Briefly, serum proteins were adhered to the solid substrate of a SELDI chip. The proteins were then desorbed by surface enhanced laser desorption in a SELDI-MS apparatus, and analyzed by mass spectrometry.

SELDI-MS was performed using a Ciphergen (Freemont, Calif.) SELDI PDSII instrument. IMAC30 chips were used, with standard sample preparation as suggested by the manufacturer. In SELD TOF (time of flight)-MS analysis, a nitrogen laser (337 nm) desorbed the protein-SPA mixture from the surface of the chip array, enabling the detection of proteins/peptides captured by the array. The mass spectra were collected by time of flight analysis based on an average of 80 laser shots, with a laser intensity that was optimized for the chip surface. The mass:charge ratio (m/z) of each protein was determined according to a variety of externally calibrated peptide and protein standards. Samples were loaded (unfractionated) onto the chips using a Beckman Robotic liquid handling system.

The SELDI-MS procedure analyzed proteins over the m/z ratio ranges of 2-20 and 20-100 kDa.

Results:

All of the patients given AES-14 by oral administration had a protein of approximately 9295 m/z that increased in concentration in serum during the period of glutamine supplementation, and decreased almost to the baseline level one week after stopping glutamine supplementation. FIG. 1 shows the profile in one typical patient of increasing abundance of this protein during treatment with glutamine. This 9.29 kDa protein did not show an increase in concentration in any of the patients receiving placebo. It appears that at least one other protein in the molecular weight range of approximately 9200 to 9350 and at least one protein with a molecular weight of approximately 9500 also increased in abundance with glutamine supplementation.

Figure 2:
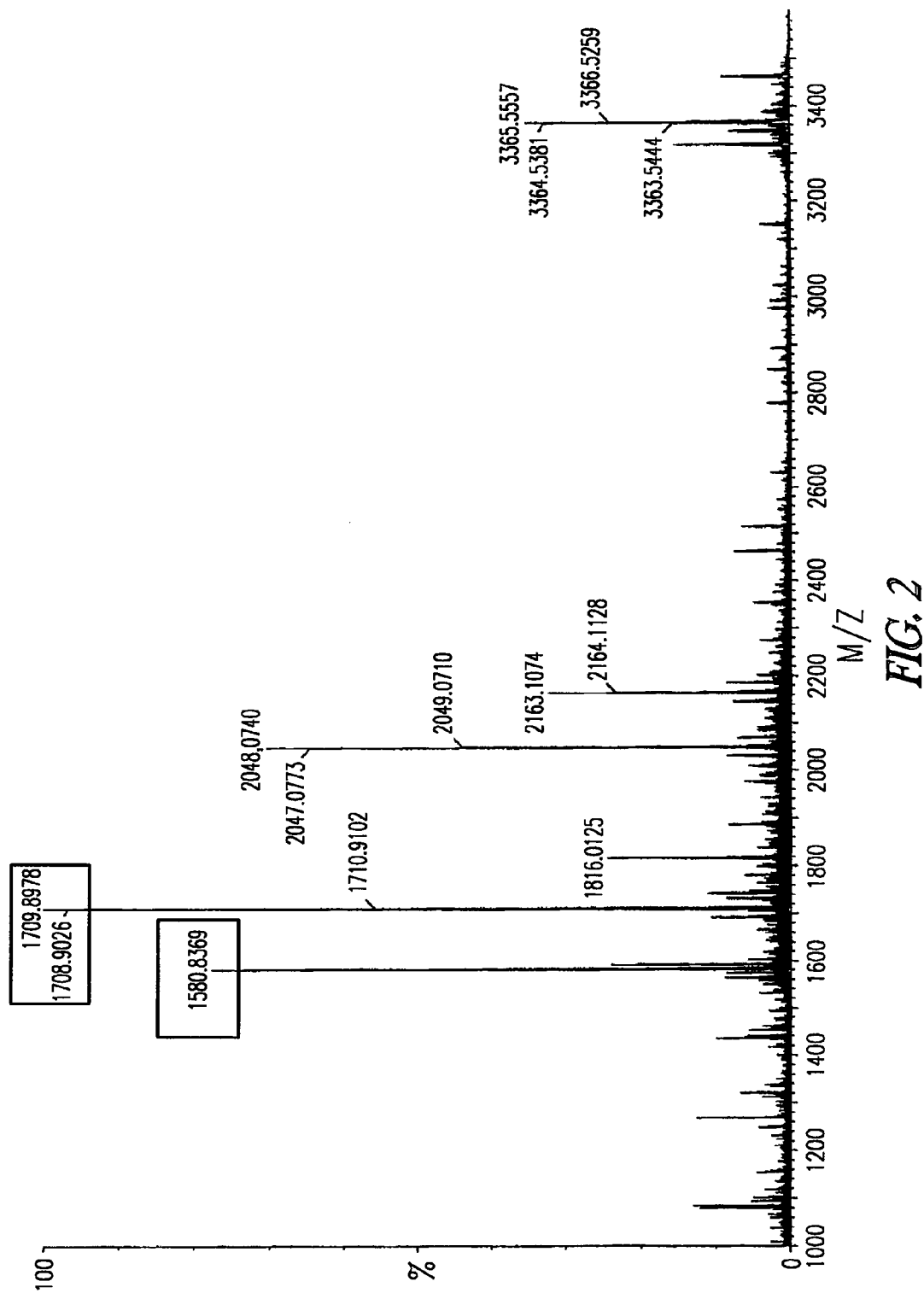
FIG. 2 shows a mass spectrometry analysis of a trypsin digest of the 9.3 kDa fraction of serum proteins isolated from a breast cancer patient receiving glutamine (AES-14) supplementation.

Serum was fractionated by SEPHADEX size-exclusion chromatography to isolate the fraction of proteins with sizes below approximately 10 kDa. This <10 kDa fraction was digested with trypsin and then analyzed by electrospray mass spectrometry. Two trypsin fragments particularly showed an increase in concentration during the period of glutamine supplementation: fragments with an m/z of about 1581 and 1710 (FIG. 2). One or both of these fragments could be a fragment of the 9.29 kDa glutamine-responsive protein.

Example 4

Polyacrylamide gel cores containing the protein of interest were cut out for digestion with trypsin, using previously published procedures. The piece of gel was destained with 100 ul of 50 mM ammonium bicarbonate; 30% v/v acetonitrile at room temperature. The destaining solution was removed and replaced with 25 ul 10 mM DTT in 50 mM ammonium bicarbonate at 56° C. Gel pieces were washed (100 ul 50 nM ammonium bicarbonate) and dried in a vacuum oven for 30 minutes. Dried gel was rehydrated in a solution 50 mM bicarbonate containing 7 ng/ul trypsin. After overnight incubation at 37° C., the gel piece was dried under high vacuum centrifugation and rehydrated in 20 ul distilled water and dried in a speed vacuum for 30 minutes.

Peptides were extracted from the dried gel with 0.1% TFA in a propylene tube. The extraction was repeated twice, and the extracts were pooled. The volume of the pooled extracts was reduced to 2-3 μl by evaporation under vacuum. Control extractions were performed on blank gel cores.

A sample (1.5 μl) was then placed on a matrix-assisted laser desorption/ionization mass spectroscopy (MALDI) 100 well target plate. Identical volumes of matrix (10 mg/ml α-cyano-4-hydroxycinnamic acid in 50% v/v acetonitrile, 0.1% v/v TFA) were added to each well. Mass measurements from liquid solution were conducted with a MALDI-TOF mass spectrometer (Applied Biosystems, Framingham, Mass.) equipped with a 337 nm laser. The analyzer was used in reflectron mode at an accelerating voltage of 20 kV, a delayed extraction parameter of 100-140 ns and a low mass gate of 1000 Da. Masses of the highest peaks were extracted from the spectra and used for protein identification using the SmartIdent peptide mass fingerprint tool. The sequences AD(I/L)AGH(Q/K)EV(I/L)R (SEQ ID NO:1) and HGTVV (I/L)T(I/L)GG(I/L)K (SEQ ID NO:2) were identified, and were queried against SWIS-PROT and TrEMBL databases. No matching human sequences were uncovered.

The invention is described with reference to various specific and preferred embodiments and techniques. However, it should be understood that many variations and modifications may be made while remaining within its scope.

All referenced publications, patents, and patent documents are hereby incorporated by reference.

What is claimed is:

1. A method of monitoring the effect of glutamine supplementation to protect the breast tissue of a breast cancer patient against radiation injury, comprising:
    monitoring the increase in the amount of serum proteins in the molecular weight range of 9100 to 9650 Da of a human afflicted with breast cancer during administration of glutamine to a patient undergoing radiation therapy;
    measuring the increase in the amount of serum proteins of a molecular weight of about 790 Da; and
    correlating the increase in the amount of said serum proteins to the extent of protection of the breast tissue of said patient against injury by said radiation by said glutamine;
    by determining if the amount of serum protein increases at least 2- to 5-fold in the first weeks of glutamine supplementation.

2. The method of claim 1 comprising monitoring the increase in the amount of serum proteins in the molecular weight range of 9100 to 9650 Da possessing trypsin digestion fragments of about 1581 Da or about 1709 Da or both.

3. The method of claim 1 wherein monitoring comprises fractionating serum proteins.

4. The method of claim 3 wherein fractionating comprises performing size exclusion chromatography.

5. The method of claim 1 wherein fractionating comprises adhering the serum proteins to a solid substrate, and then desorbing and fractionating the serum proteins from the solid substrate by Surface Enhanced Laser Desorption ionization Mass Spectrometry.

6. The method of claim 1 wherein the serum proteins are monitored before, during, and after radiation therapy.

* * * * *

UNITED STATES PATENT AND TRADEMARK OFFICE
CERTIFICATE OF CORRECTION

PATENT NO. : 8,268,573 B2
APPLICATION NO. : 12/538987
DATED : September 18, 2012
INVENTOR(S) : Suva et al.

Page 1 of 1

It is certified that error appears in the above-identified patent and that said Letters Patent is hereby corrected as shown below:

In the Specification

In column 2, line 37, after "PAGE" insert --gel.--, therefor

In the Claims

In column 9, line 39, in claim 1, delete "790" and insert --9290--, therefor

In column 9, line 45, in claim 1, after "first", insert --two--, therefor

In column 10, line 40, in claim 5, delete "ionization" and insert --Ionization--, therefor Signed and Sealed this
Twenty-fourth Day of November, 2015

Michelle K. Lee
*Director of the United States Patent and Trademark Office*